(12) United States Patent
Huettenbrink et al.

(10) Patent No.: US 10,278,813 B2
(45) Date of Patent: May 7, 2019

(54) OSSICULAR PROSTHESIS COMPRISING FOLDABLE HEAD PLATE

(71) Applicant: Heinz Kurz GmbH Medizintechnik, Dusslingen (DE)

(72) Inventors: Karl-Bernd Huettenbrink, Dresden (DE); Axel Lang, Reutlingen (DE); Uwe Steinhardt, Hirrlingen (DE); Markus Gaeckle, Bad Liebenzell (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 3 days.

(21) Appl. No.: 15/786,800

(22) Filed: Oct. 18, 2017

(65) Prior Publication Data

US 2018/0104048 A1 Apr. 19, 2018

(30) Foreign Application Priority Data

Oct. 19, 2016 (DE) .................. 20 2016 105 874

(51) Int. Cl.
*A61F 2/18* (2006.01)
*A61L 27/04* (2006.01)
(Continued)

(52) U.S. Cl.
CPC .............. *A61F 2/18* (2013.01); *A61L 27/042* (2013.01); *A61L 27/06* (2013.01); *A61L 27/54* (2013.01);
(Continued)

(58) Field of Classification Search
CPC ................................................ A61F 2002/183
See application file for complete search history.

(56) References Cited

U.S. PATENT DOCUMENTS 5,397,331 A * 3/1995 Himpens ............ A61B 17/0057
128/899
5,999,632 A * 12/1999 Leysieffer ................. A61F 2/18
181/130
(Continued)

FOREIGN PATENT DOCUMENTS

DE    19744789         4/1998
DE    19647579 A1 *   5/1998  ............... A61F 2/18
(Continued)

OTHER PUBLICATIONS

M.W. Yung, Ph.D., F.R.C.S., D.L.O., C. Brewis, F.R.C.S., "A comparison of the user-friendliness of hydroxyapatite and titanium ossicular prostheses", The Journal of Laryngology & Otology, Feb. 2002, vol. 116, pp. 97-102.
(Continued)

*Primary Examiner* — David H Willse
*Assistant Examiner* — Javier G Blanco
(74) *Attorney, Agent, or Firm* — Collard & Roe, P.C.

(57) ABSTRACT

An ossicular prosthesis has a head plate as a first fastening element, a second fastening element for the mechanical connection to the ossicular chain, or to the inner ear, and a connecting element. The head plate has a central coupling region and radially outward extending bridging elements which are connected to the coupling region via a radially inner end region and each transition into an outer free end section. The bridging elements are connected to the coupling region so that they fold together upon introduction of a force component parallel to the longitudinal axis, wherein their end sections are pivoted radially closer to the longitudinal axis and thereby also execute an axial movement. The bridging elements, without this force, extend from the coupling region at a predefined, fixed angle. The prosthesis
(Continued)

can be inserted into the middle ear of the patient more easily and through a much smaller artificial opening.

9 Claims, 8 Drawing Sheets

(51) Int. Cl.
*A61L 27/06* (2006.01)
*A61L 27/54* (2006.01)
*A61B 17/12* (2006.01)

(52) U.S. Cl.
CPC ..... *A61B 17/1215* (2013.01); *A61F 2002/183* (2013.01); *A61L 27/045* (2013.01)

(56) References Cited

U.S. PATENT DOCUMENTS

| | | | |
|---|---|---|---|
| 6,398,717 B1* | 6/2002 | Leysieffer | H04R 25/606 600/25 |
| 6,554,861 B2 | 4/2003 | Knox et al. | |
| 6,579,317 B2 | 6/2003 | Kurz | |
| 6,605,112 B1* | 8/2003 | Moll | A61F 2/2412 623/1.24 |
| 7,806,931 B2 | 10/2010 | Huettenbrink et al. | |
| 2004/0162614 A1* | 8/2004 | Steinhardt | A61F 2/18 623/10 |
| 2006/0271190 A1 | 11/2006 | Reitan et al. | |
| 2008/0234817 A1* | 9/2008 | Huettenbrink | A61F 2/18 623/10 |
| 2009/0240330 A1* | 9/2009 | Steinhardt | A61F 2/18 623/10 |
| 2009/0240331 A1* | 9/2009 | Steinhardt | A61F 2/18 623/10 |
| 2009/0240332 A1* | 9/2009 | Steinhardt | A61F 2/18 623/10 |
| 2012/0197066 A1* | 8/2012 | Abel | H04R 25/606 600/25 |
| 2013/0018217 A1* | 1/2013 | Santek | H04R 25/606 600/25 |
| 2014/0303728 A1* | 10/2014 | Steinhardt | A61F 2/18 623/10 |
| 2017/0156853 A1 | 6/2017 | Weber et al. | |

FOREIGN PATENT DOCUMENTS

| | | |
|---|---|---|
| DE | 20 2005 003 782 U1 | 5/2005 |
| DE | 10 2007 013 708 B3 | 1/2008 |
| EP | 1 181 907 B1 | 5/2004 |
| SU | 787021 | 12/1980 |
| SU | 957894 | 9/1982 |
| WO | 02/069850 A1 | 9/2002 |
| WO | 2016/005946 A2 | 1/2016 |

OTHER PUBLICATIONS

German Office Action in DE 10 2016 119 943.5 dated Jul. 21, 2017 with English translation of relevant parts.

* cited by examiner

OSSICULAR PROSTHESIS COMPRISING FOLDABLE HEAD PLATE

CROSS REFERENCE TO RELATED APPLICATIONS

Applicant claims priority under 35 U.S.C. § 119 of German Application No. 20 2016 105 874.0 filed on Oct. 19, 2016, the disclosure of which is incorporated by reference.

BACKGROUND OF THE INVENTION

The invention relates to an ossicular prosthesis which replaces or bridges at least one member or parts of a member of the ossicular chain, wherein the ossicular prosthesis comprises, at its one end, a first fastening element in the form of a head plate which is intended to mechanically rest against the tympanic membrane and/or against the malleus handle and, at its other end, a second fastening element for the mechanical connection to one member or parts of a member of the ossicular chain, or to the inner ear, and a connecting element which connects the two fastening elements to one another in a sound-conducting manner along a longitudinal axis, and wherein the head plate comprises a radially inner coupling region situated centrally with respect to the longitudinal axis for the mechanical coupling of the head plate to the connecting element, and multiple bridging elements extending outwardly from the central coupling region, radially away from the longitudinal axis, each of which is connected to the central coupling region via a radially inner end region and transitions into a radially outer, free end section. A device of this type is known from DE 10 2007 013 708 B3.

Ossicular prostheses are used in cases in which the ossicles of the human middle ear are missing or damaged, either entirely or partially, in order to conduct sound from the tympanic membrane to the inner ear. The ossicular prosthesis has two ends in this case, wherein, depending on the specific conditions, one end of the ossicular prosthesis rests against the tympanic membrane or against the malleus handle, for example by means of a head plate, and the other end of the ossicular prosthesis is fastened, for example, to the stapes of the human ossicular chain, or is inserted directly into the inner ear. In the known ossicular prostheses, sound conduction between the tympanic membrane and the inner ear is often limited because the ossicular prostheses cannot fully replace the natural anatomical formations of the ossicular chain.

After the prosthesis has been surgically implanted in the middle ear and the tympanic membrane has been closed, the so-called recovery phase begins. Scars form during this period, and they produce unforeseeable forces which can cause the prosthesis to move out of its local position. When there is a stiff connection between the head plate and the shaft, increased pressure peaks can result between the edge of the head plate and the tympanic membrane or the graft between the tympanic membrane and the head plate. These pressure peaks can be so high that penetration or extrusion through the tympanic membrane would result. For this reason, it is very helpful when the prosthesis has a certain postoperative mobility, so that the head plate can automatically adapt, postoperatively, to the position of the tympanic membrane.

Since, in addition, the unique anatomical features of the ear, such as the position, shape and size of the stapes, incus, hammer and tympanic membrane, vary, it is highly advantageous when ossicular prostheses do not have a rigid configuration, but rather have a certain amount of flexibility or variability.

In order to attain this level of flexibility/variability, it is known to use various fastening and coupling devices for ossicles, which have elastic parts and/or articulations. Such an articulated connection between a fastening element, which can be installed on the stapes footplate, and the elongate shaft is described, for example, in EP 1 181 907 B1, and is offered by the applicant under the trade mark "Ball-Joint".

A further complication that occasionally arises is caused by inadequate ventilation of the middle ear space and the associated inflammation, tumor formation, adhesions in the region of the tympanic membrane, and stiffening thereof. When the eustachian tube malfunctions, for example, underpressure may form in the middle ear, which can cause the tympanic membrane to protrude (or retract), thereby resulting in adhesion with the stapes, for example. In order to counteract this, and in order to enable postoperative movements of the tympanic membrane to be followed, the head plates of known ossicular prostheses are designed to be tiltable relative to the connecting element which connects the head plate to the second fastening element and is usually designed as an elongate shaft. A head plate of this type, which is rigid yet tiltable relative to the connecting element, is described, inter alia, in US 2004/0162614 A1, in the article M. W. YUNG, Ph.D., F. R. C. S., D. L. O., C. BREWIS, F. R. C. S., "A comparison of the user-friendliness of hydroxyapatite and titanium ossicular prostheses", The Journal of Laryngology & Otology, February 2002, Vol. 116, pp. 97-102, or, for example, in US 2006/0271190 A1.

DE 20 2005 003 782 U1 describes an ossicular prosthesis, in which the head plate comprises an integrated ball joint which is connected to the connecting shaft of the two fastening elements.

The disadvantage of these known ossicular prostheses, however, is that, due to the rigid tilting of the head plate that occurs in the event of local medial movements of the tympanic membrane, the opposite side of the head plate is simultaneously moved laterally outward, thereby generating pressure peaks on the tympanic membrane.

Finally, DE 10 2007 013 708 B3, which was cited at the outset, discloses an ossicular prosthesis of the type in question, which comprises a head plate having a highly flexible configuration, in the case of which the advantages of the prosthesis according to the aforementioned document DE 20 2005 003 782 U1, on the one hand, and, on the other hand, the advantages of the prostheses described in US 2004/0162614 A1 and US 2006/0271190 A1 are retained, wherein, however, the shared disadvantages of a rigid tilting of the head plate are avoided. One problem associated with the ossicular prosthesis according to DE 10 2007 013 708 B3, however, is its insertion into the middle ear of the patient, because the head plate protrudes laterally outward to a considerable extent, in particular in the radial direction relative to its longitudinal axis, and can only be surgically inserted through the tympanic membrane region into the middle ear by means of a large artificial opening. This large opening then also has a more difficult time healing postoperatively, of course, and also leaves correspondingly large scars.

SUMMARY OF THE INVENTION

The problem addressed by the present invention is therefore that of improving a device of the type in question, and as described at the outset, using the simplest technical means possible in such a way that a high level of postoperative flexibility and variability of the prosthesis is attained in a simple and cost-effective manner while ensuring good sound conduction, wherein the advantages described in DE 10 2007 013 708 B3 are to be retained but the prosthesis is designed in such a way that it can be inserted into the middle ear of the patient substantially more easily and through a much smaller artificial opening.

According to the invention, this problem is solved in a surprisingly simple yet effective manner in that the bridging elements are connected, at their end regions situated radially inward relative to the longitudinal axis, to the central coupling region in such a way that they fold upward or downward, in the manner of an umbrella, in the direction of the longitudinal axis upon introduction of a force having a force component parallel or antiparallel to the longitudinal axis, wherein their radially outward, free end sections are each pivoted, relative to the longitudinal axis, toward a position located radially closer to the longitudinal axis and thereby also execute an axial movement relative to the longitudinal axis, and the bridging elements, without introduction of this force, extend from the central coupling region at a predefined, fixed angle relative to the longitudinal axis.

As a result, the advantages of the above-described ossicular prosthesis of the type in question, as is described in DE 10 2007 013 708 B3, are retained in a relatively simple way. Due to the possibility of an umbrella-like folding open and folding closed of the bridging elements which, according to the invention, do not extend into a radially outer annular region but rather each terminate in a free radial end section, the prosthesis according to the invention, during implantation into the human middle ear, can also be easily inserted through a very small opening in the tympanic membrane. Due to a minimal opening in the tympanic membrane, the preload on the tympanic membrane is naturally retained to the greatest possible extent. As a result, better sound transmission as well as faster recovery and healing are expected. It may also be possible to enter the middle ear using an endoscope, through a natural opening in the eustachian tube, and thereby position a "folded" prosthesis.

A particularly preferred embodiment of the ossicular prosthesis according to the invention is distinguished by the fact that bridging elements, in a state without introduction of force, extend from the central coupling region in an angle range relative to the longitudinal axis between 80° and 100°, preferably approximately at a right angle. Preset angles in the relaxed state can therefore better replicate the natural shape of the tympanic membrane, which is usually not planar, and form a support surface having the largest possible area, for better sound transmission.

In one class of alternative embodiments, the bridging elements extend, in a state without introduction of force, from the central coupling region at different, predefined angles relative to the longitudinal axis. In this case, it is conceivable, for example, that the malleus handle is also integrated into the prosthesis support surface on the tympanic membrane.

Refinements of this class of embodiments are particularly advantageous, in which the predefined angles of the bridging elements, in a state without introduction of force, are selected in such a way that the first fastening element replicates the anatomical shape of the tympanic membrane.

Yet another class of relatively simple embodiments of the invention is distinguished by the fact that the radially inner end regions of the bridging elements are in the form of mechanical articulations. The mechanical articulations allow for a highly specific angling of the bridging elements and, therefore, a pivot point located close to the shaft. The prosthesis can therefore be folded very "tightly".

One class of alternative embodiments, in which at least the radially inner end regions of the bridging elements are formed from an elastic, flexible material, is more elegant and is considerably less expensive to produce. When the inner end regions of the bridging elements consist of a flexible material, the prosthesis, mutatis mutandis, can be folded even more "tightly" than is the case with mechanical rotational joints. The space and the technical complexity required for the mechanical rotational joints are then reduced.

In particularly advantageous refinements of this class of embodiments, the elastic, flexible material of the radially inner end regions has an elasticity≥1%, preferably an elasticity≥2%. If the material of the inner end points has a flexibility>1%, the prosthesis can be folded particularly "tightly", and so it is nevertheless ensured that the prosthesis, when unfolded, returns again to the "original state". As a result, it is also ensured that the prosthesis follows the smallest "topographical" changes in the tympanic membrane.

This can be attained by a class of variants in that the elastic, flexible material of the radially inner end regions contains highly elastic material, preferably amorphous metal, in particular based on nickel, iron, cobalt, or zirconium, and/or a nickel/titanium alloy. The aforementioned properties of the flexibility, in combination with stiffness that is good for sound conduction, can be optimally attained with the aid of the aforementioned materials.

Alternatively, however, the elastic, flexible material of the radially inner end regions can contain highly elastic plastic, in particular a high-strength elastic polymer, and/or elastic ceramic. These materials provide for ideal preconditions for good sound transmission, in combination with high flexibility and good stiffness but with lesser density.

An embodiment of the ossicular prosthesis according to the invention is particularly preferred in which the radially outer, free end sections of the bridging elements have atraumatic, non-sharp, radially outer—relative to the longitudinal axis—free end edges which expand transversely relative to the direction of the longitudinal axis. In this way, in the event of a tilting moment occurring in the healing phase, which results in an increased force effect on the outer end sections, the surface pressure and the risk of extrusion can be reduced.

Further advantageous refinements of the ossicular prosthesis according to the invention are distinguished by the fact that the radially outer, free end sections of the bridging elements are formed as atraumatic surfaces, preferably as closed surfaces or annular surfaces, in particular having a circular or elliptical configuration.

Embodiments of the invention are also preferred in which the bridging elements extend between the central coupling region and its particular radially outer, free end section not rectilinearly but rather in the shape of a curve, thereby enhancing the desired effect of local flexibility of the head plate, and ensuring that deflections are limited to a local region in the event of relatively small medial movements of the tympanic membrane. In addition, the head plate can therefore more easily follow any postoperative change in the tympanic membrane.

In further advantageous embodiments of the ossicular prosthesis according to the invention, the bridging elements are each formed entirely from an elastic material. As a result, it is possible to maintain a bending radius that tends to be greater, and to therefore prevent a plastic, permanent deformation of the prosthesis.

Generally, in the case of the ossicular prosthesis according to the invention, the head plate is situated at one end of an elongate shaft which connects the head plate to the other end of the ossicular prosthesis, as is well known from the related art. In order to attain the above-described flexibility and variability of the prosthesis, as described per se in EP 1 181 907 B1, in a particularly preferred embodiment, at least one ball joint can be provided on or in the elongate shaft. With respect to particularly high postoperative mobility of the prosthesis, refinements are advantageous in which the elongate shaft includes a large number of further rotary elements which abut one another, preferably in the form of a ball joint chain. Alternatively, in particularly simple embodiments of the inventive prosthesis that can be cost-effectively produced, the shaft can also have an integrally continuous, in particular rigid, configuration.

The prosthesis will be designed according to the particular defect to be eliminated or at least ameliorated in terms of its effect on the patient via use of the ossicular prosthesis according to the invention. In all embodiments of the invention, the first fastening element will include a head plate designed to rest against the tympanic membrane and/or against the malleus handle. In many embodiments, one side of the prosthesis can be fastened, for example, to the limb of incus or to the stapes, or it may be inserted directly into the inner ear. In this context, an embodiment is advantageous in which the ossicular prosthesis is situated at the end of the hammer (=umbo) or directly adjacent thereto, thereby resulting in the greatest leverage for the mechanical transmission of sound via motions that occur in the artificial or natural ossicular chain.

One class of embodiments of the ossicular prosthesis according to the invention is distinguished by the fact that the second fastening element is in the form of a plate, a socket, a loop, a closed bell, a singly or multiply slotted bell, or a clip for mechanical connection to a further member of the ossicular chain. In refinements of these embodiments, the prosthesis rests, on one side, against the tympanic membrane and/or the malleus handle via the head plate and, on the other side, is fastened to the incus or to the stapes via the second fastening element. Alternative embodiments can provide that the ossicular prosthesis is connected, at its end at which the second fastening element is located, directly to the inner ear, in particular via a piston, by means of perforation of the stapes footplate (stapedectomy or stapedotomy), and/or by means of opening the human cochlea (=cochleotomy).

In addition to the postoperative shifting of position, a further problem results after the implantation of ossicular prostheses: The middle ear of the human body can be described as a "semi-open region". Any implantation material that is inserted into the body within the scope of reconstruction of the middle ear and its structures thereby undergoes a particular stress in that a contaminated and infected environment prevails, which generally attacks the material. Since the objective of implanting an ossicular prosthesis must always be to enable the implant to remain in the patient's middle ear for as long as possible without complications occurring, a sustained attack on the material can result in damage being done to the prosthesis and/or in a local infection. Neither of these consequences is tolerable. In yet another particularly preferred embodiment of the invention, in order to permanently prevent damage from occurring to the implantation material or the surrounding tissue, the surface of the ossicular prosthesis is coated entirely or at least in sections with a biologically active coating, in particular a growth-inhibiting and/or growth-promoting and/or antibacterial coating. The head plate of the ossicular prosthesis according to the invention should always comprise a growth-promoting coating, but a second fastening element that leads directly into the inner ear, which is designed approximately in the form of a piston, should have a growth-inhibiting coating.

The ossicular prosthesis according to the invention, or parts thereof, can be produced from titanium and/or from gold and/or from tantalum and/or from steel, and/or from an alloy of the aforementioned metals. It is known that titanium, in particular, in addition to being stiff and having excellent sound-conducting properties, also exhibits excellent biocompatibility with the human middle ear. With respect to the aforementioned postoperative position adjustment, embodiments of the invention are advantageous in which the prosthesis or parts thereof—in particular one of the fastening elements—is/are produced from a material having memory effect or superelastic properties, preferably Nitinol, as is known per se, for example, from WO 02/069850 A1 or U.S. Pat. No. 6,554,861 B2.

Alternatively or additionally, in further embodiments, parts of the ossicular prosthesis according to the invention can be produced from a ceramic material. Embodiments of the invention are also possible, in which the prosthesis or parts thereof are produced from biocompatible plastics, in particular silicone, polytetrafluoroethylene (PTFE), or fibrous composite materials. These materials also make it possible to prevent postoperative rejection reactions in most cases.

Finally, yet another embodiment of the invention is distinguished by the fact that the prosthesis is connected to an active vibrating part of an active, in particular implantable, hearing aid. This also enables further hearing damage caused by the use of modern electronic devices in many areas to be eliminated or at least substantially ameliorated in terms of its effect, wherein, due to the above-described coating, a physical connection of the prosthesis to the outside world, in turn, does not cause any problems resulting from an increased introduction of bacteria into the region of the middle ear when the coating correspondingly has an antibacterial design.

The scope of the present invention also includes a system comprising an ossicular prosthesis according to one of the preceding claims, and an implantation aid comprising an elongate hollow body which is open on at least one side and which is distinguished by the fact that its internal width is selected in such a way that the ossicular prosthesis, in a state with introduction of force onto the bridging elements, can be accommodated entirely or partially in the hollow body. A lesser trauma is advantageous in this case, since only a smaller opening of the tympanic membrane, etc., is necessary.

This system can be further improved by way of the hollow body being in the form of a minimally invasive, in particular endoscopic, instrument, which is preferably tubular or hose-shaped. As a result, an introduction via natural connections or openings such as, for example, the eustachian tube, is also possible.

Further features and advantages of the invention will become apparent from the detailed description of exemplary embodiments of the invention which follows, with reference to the figures in the drawing, which shows the details that are essential to the invention. Further features and advantages of the invention will also become apparent from the claims.

The individual features can be implemented individually, or they can be combined in any possible manner to form variants of the invention.

BRIEF DESCRIPTION OF THE DRAWINGS

Exemplary embodiments of the invention are represented in the schematic drawing and are described in greater detail in the description which follows.

In the drawing.

DETAILED DESCRIPTION OF THE EMBODIMENTS

The embodiments of ossicular prostheses 10; 20; 30 represented schematically in FIGS. 1a to 4b each comprise, at one end, a first fastening element 11; 21; 31 which is designed in the form of a head plate which is intended to rest against the tympanic membrane and/or against the malleus handle. Attached to the other end of each of the ossicular prostheses 10; 20; 30 is a second fastening element 12; 22; 32 for mechanically connecting the prosthesis to one member or parts of a member of the ossicular chain, or to the inner ear. Situated therebetween is a connecting element 13; 23; 33 which connects the two fastening elements 11, 12 and 21, 22 and 31, 32, respectively, along a longitudinal axis z in a sound-conducting manner and which can be designed approximately in the form of an elongate shaft.

The head plates of the ossicular prostheses 10; 20; 30 have a central coupling region 14; 24; 34, respectively, for the mechanically coupling of the head plate to the connecting element 13; 23; 33, and comprise multiple bridging elements 15; 25; 35 which extend outward from the central coupling region 14; 24; 34, radially away from the longitudinal axis z, and are each connected to the central coupling region 14; 24; 34 via a radial inner end region 16; 26; 36, respectively, and each transitions into a radially outer, free end section 17; 27; 37, respectively. Generally, the bridging elements 15; 25; 35 are geometrically designed in such a way that, in the event of a local medial movement of the tympanic membrane, the bridging elements follow this medial movement locally but do not transmit the movement to remote regions of the head plate.

The invention is distinguished from known ossicular prostheses of the type in question in that the bridging elements 15; 25; 35 are connected, at their end regions 16; 26; 36 situated radially inward relative to the longitudinal axis z, to the central coupling region 14; 24; 34 in such a way that they fold upward or downward, in the manner of an umbrella, in the direction of the longitudinal axis z upon introduction of a force having a force component parallel or antiparallel to the longitudinal axis z, wherein their radially outward, free end sections 17; 27; 37 are each pivoted, relative to the longitudinal axis z, toward a position located radially closer to the longitudinal axis z and thereby also execute an axial movement relative to the longitudinal axis z and, without introduction of this force, the bridging elements 15; 25; 35 extend from the central coupling region 14; 24; 34 at a predefined, fixed angle relative to the longitudinal axis z.

Figure 1A:
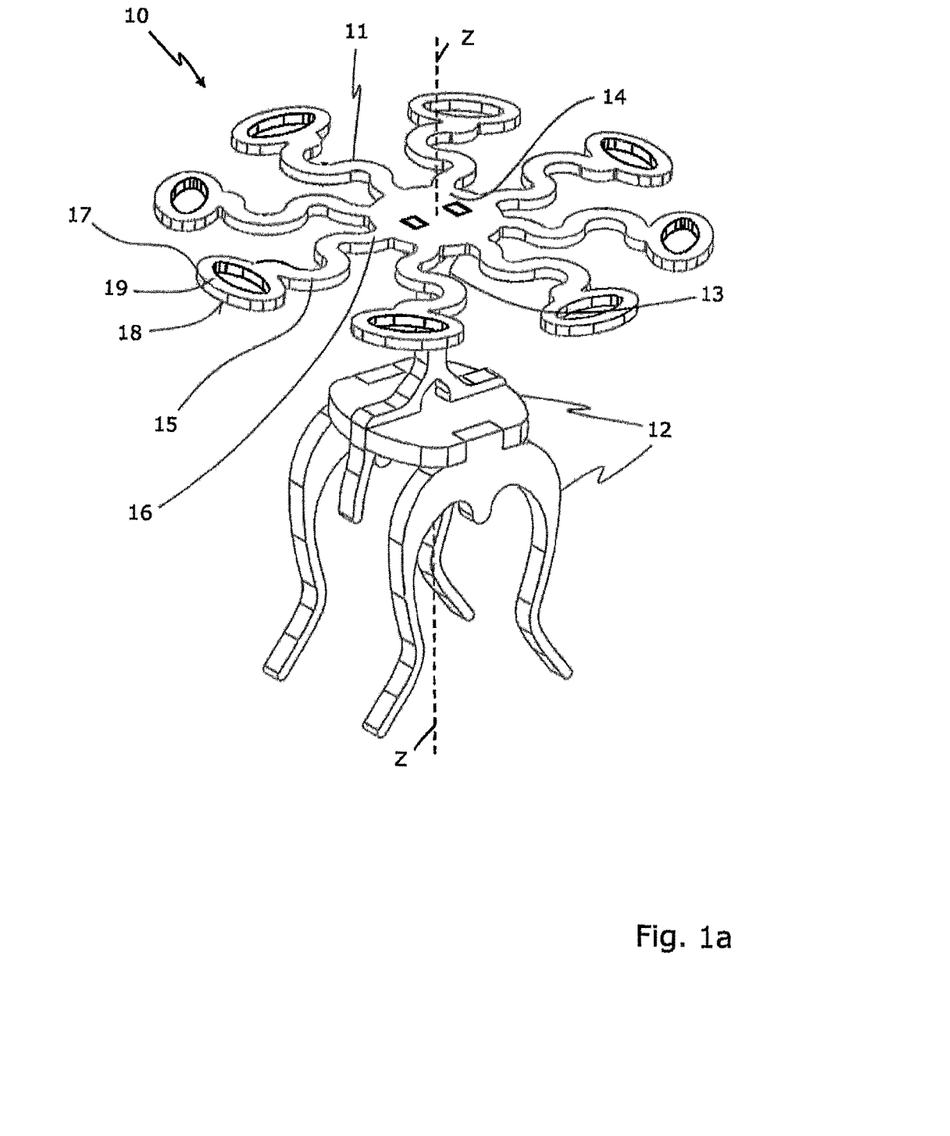
FIG. 1a shows a schematic spatial representation of a first embodiment of the ossicular prosthesis according to the invention in a top view of the head plate, diagonally from above, wherein all bridging elements lie in the head-plate plane and the second fastening element is designed as a four-fold clamp.
Figure 1B:
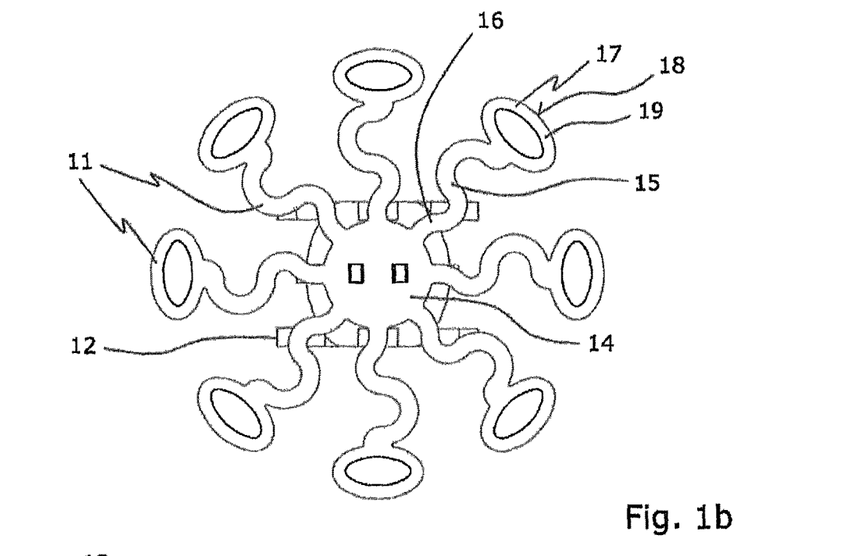
FIG. 1b shows the embodiment according to FIG. 1a in a schematic top view from above in the direction of the longitudinal axis.
Figure 1C:
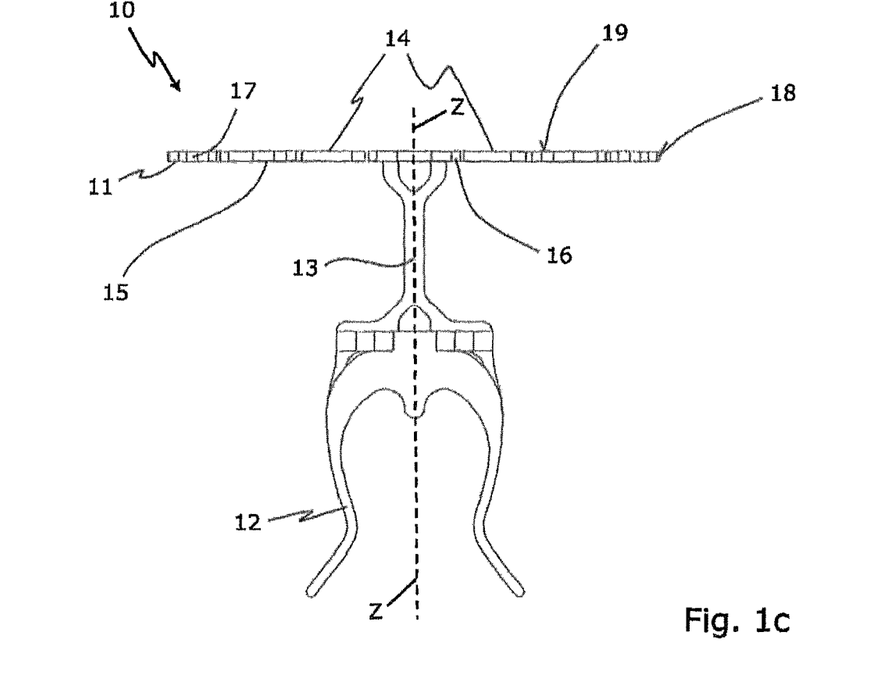
FIG. 1c shows the embodiment according to FIG. 1a in a schematic view from the side, perpendicular to the longitudinal axis.
Figure 1D:
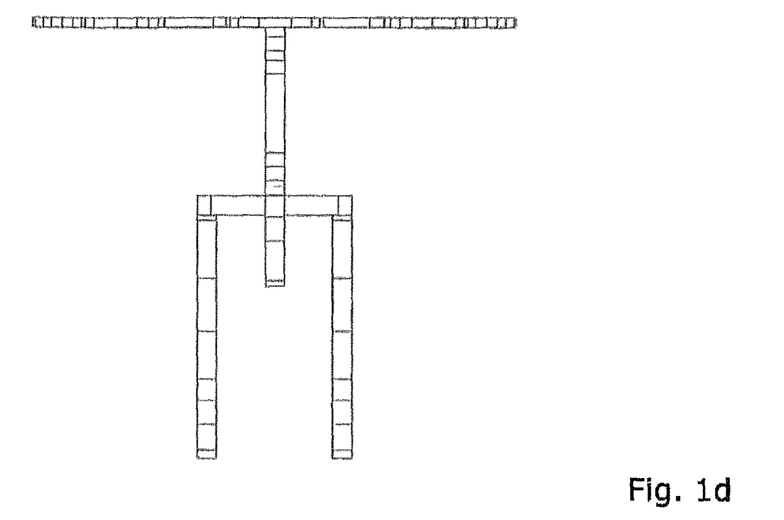
FIG. 1d is the same as FIG. 1c, but rotated through 90° about the longitudinal axis.
Figure 1E:
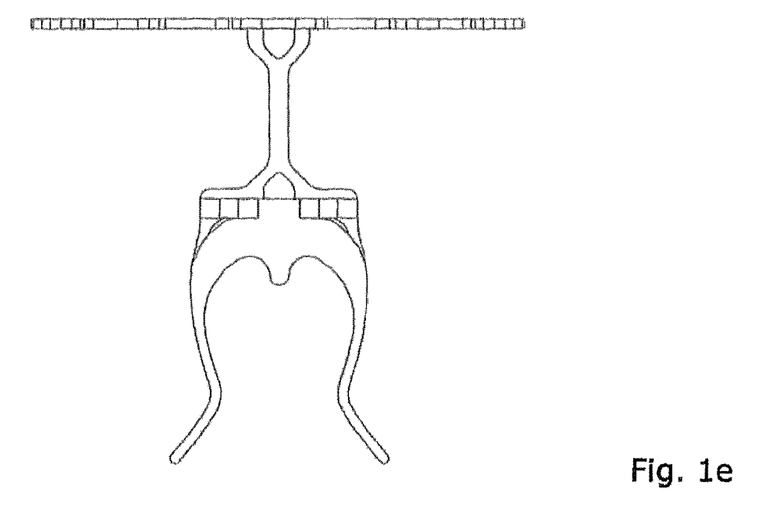
FIG. 1e shows a section in the vertical plane through the embodiment according to FIG. 1d.
Figure 2A:
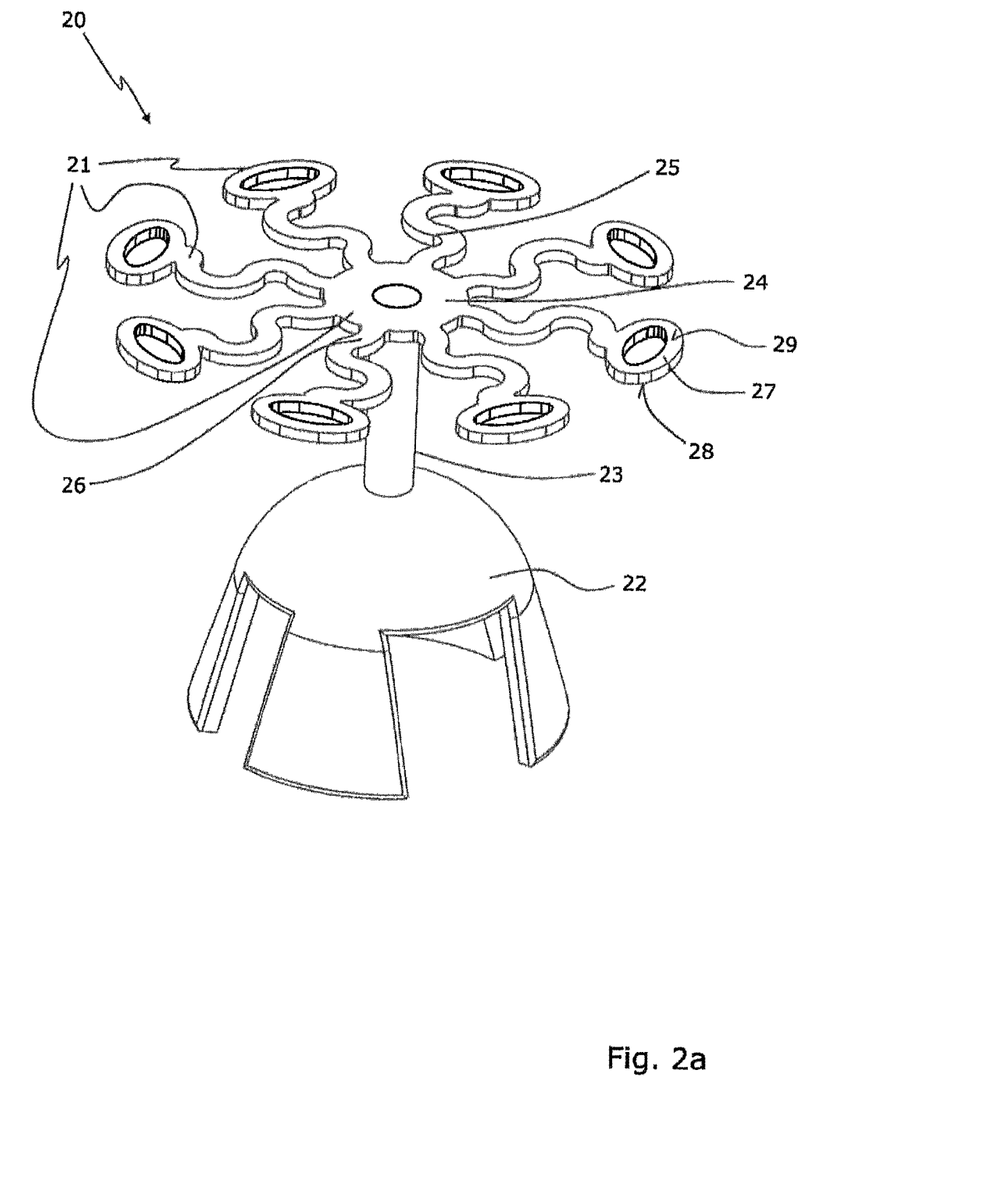
FIG. 2a shows a second embodiment, in which the bridging elements are situated at different angles with respect to the head-plate plane and the second fastening element is designed as a slotted bell.
Figure 2B:
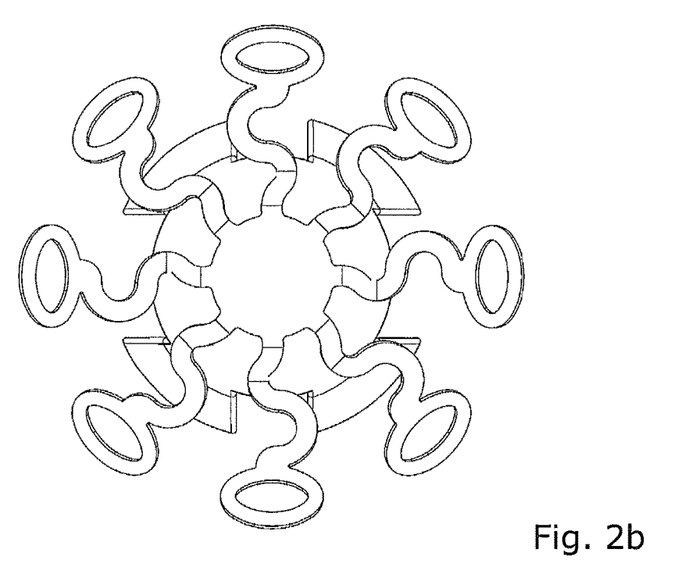
FIG. 2b shows the embodiment according to FIG. 2a in a schematic top view from above in the direction of the longitudinal axis.
Figure 2C:
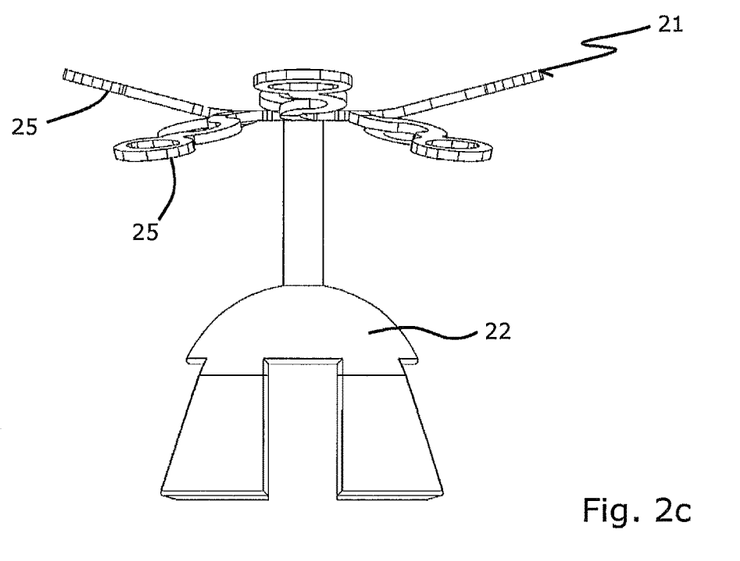
FIG. 2c shows the embodiment according to FIG. 2a in a schematic view from the side, perpendicular to the longitudinal axis.

This fixed angle relative to the longitudinal axis z can be selected, in particular, between 80° and 100°, preferably being selected to be approximately 90°, as shown on the basis of the embodiments in FIGS. 1a-1e and 3a-3c. Alternatively, in a state without introduction of force, the bridging elements 25 can also extend from the central coupling region 24 at different, predefined angles relative to the longitudinal axis z, as shown in FIGS. 2a-2c. In the latter case, the angles are preferably selected in such a way that the first fastening element 21 replicates the anatomical shape of the tympanic membrane.

Figure 3A:
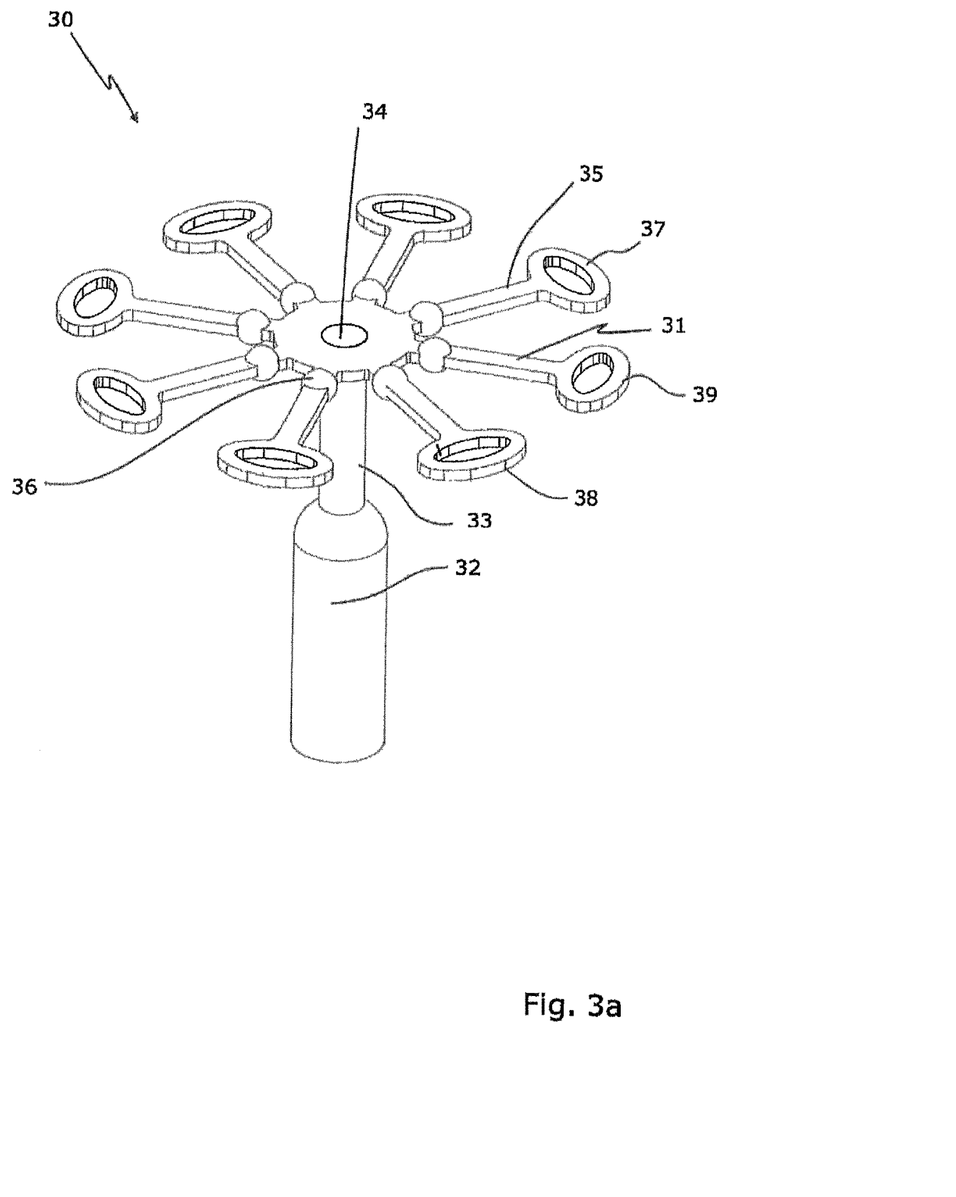
FIG. 3a shows a third embodiment, in which the bridging elements are situated in the head-plate plane and have a rectilinear configuration and are attached to the coupling region via articulations, and wherein the second fastening element is designed as a piston.
Figure 3B:
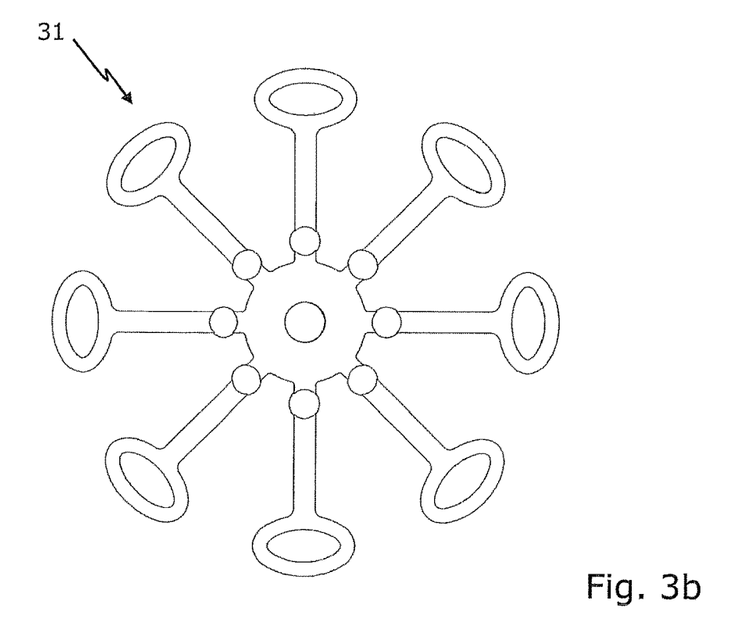
FIG. 3b shows the embodiment according to FIG. 3a in a schematic top view from above in the direction of the longitudinal axis.
Figure 3C:
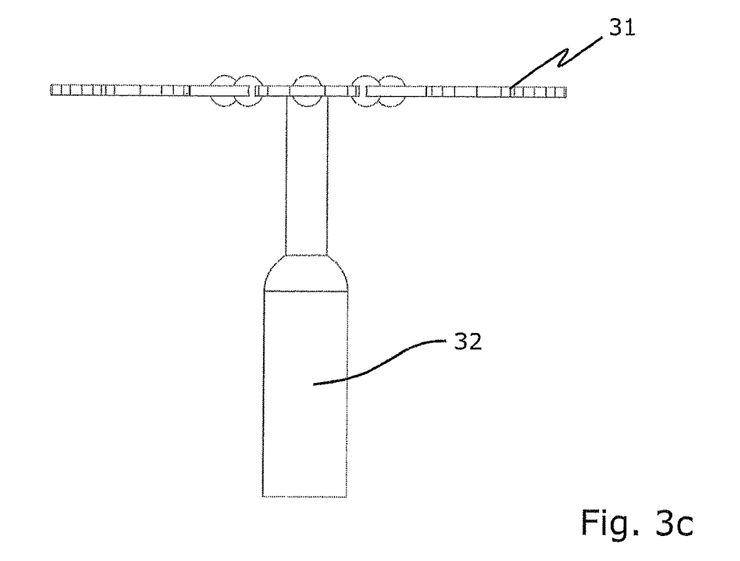
FIG. 3c shows the embodiment according to FIG. 3a in a schematic view from the side, perpendicular to the longitudinal axis.

As shown in FIGS. 3a-3c, in embodiments of the ossicular prosthesis 30 according to the invention, the radially inner end regions of the bridging elements 35 can be in the form of mechanical articulations 36.

Alternatively, in another class of embodiments, for which examples are shown in FIGS. 1a-1e and 2a-2c, at least the radially inner end regions 16; 26 of the bridging elements 15; 25 are formed from an elastic, flexible material, in particular having an elasticity≥1%, preferably having an elasticity≥2%. This material can contain amorphous metal, in particular based on nickel, iron, cobalt, or zirconium, and/or a nickel-titanium alloy, but also highly elastic plastic, in particular a high-strength elastic polymer, and/or elastic ceramic.

Moreover, all the bridging elements 15; 25; 35 can also be formed in entirety from an elastic material.

The bridging elements 35 of the embodiments according to FIGS. 3a-3c extend rectilinearly. Alternatively, in the embodiments represented in FIGS. 1a-2c, the bridging elements 15; 25 do not extend between the central coupling region 14; 24 and its radially outer, free end section 17; 27, respectively, rectilinearly, but rather in the shape of a curve, preferably in multiply deflected curves. The bridging elements 15; 25; 35 have a maximum width b and the head plates have a minimum diameter D, wherein b≤0.05 D, preferably b≈0.03 D.

In all embodiments of the ossicular prosthesis 10; 20; 30 according to the invention that are represented in the drawing, the radially outer, free end sections 17; 27; 37 of the bridging elements 15; 25; 35 have atraumatic, non-sharp, radially outer—relative to the longitudinal axis z—free end edges 18; 28; 38 which expand transversely relative to the direction of the longitudinal axis z. Additionally, these free end sections 17; 27; 37 can be in the form of atraumatic surfaces 19; 29; 39, preferably closed surfaces or annular surfaces, in particular having a circular or elliptical configuration.

The second fastening element 12; 22; 32 on the end of the ossicular prosthesis 10; 20; 30—according to the invention—opposite the head plate can be configured somewhat differently depending on the requirements of the specific application site and the corresponding anatomical conditions.

FIGS. 1a-1e show one embodiment of the invention, in which a four-legged clip was selected as the second fastening element 12.

In the embodiment according to FIGS. 2a-2c, however, the second fastening element 22 has a bell-like configuration having slots and is used to optimally fasten the ossicular prosthesis 20 to another member of the ossicular chain, for example to the incus or to the stapes.

In the present exemplary embodiment according to FIGS. 3a-3c, in turn, the second fastening element 32 is in the form of a piston for directly coupling the ossicular prosthesis 30 to the inner ear.

The mass distribution of the individual parts of the ossicular prosthesis 10; 20; 30 according to the invention can be calculated as a function of a desired, predefinable frequency response of the sound conduction in the middle ear, in order to enable the sound conduction properties to be individually tuned.

Figure 4A:
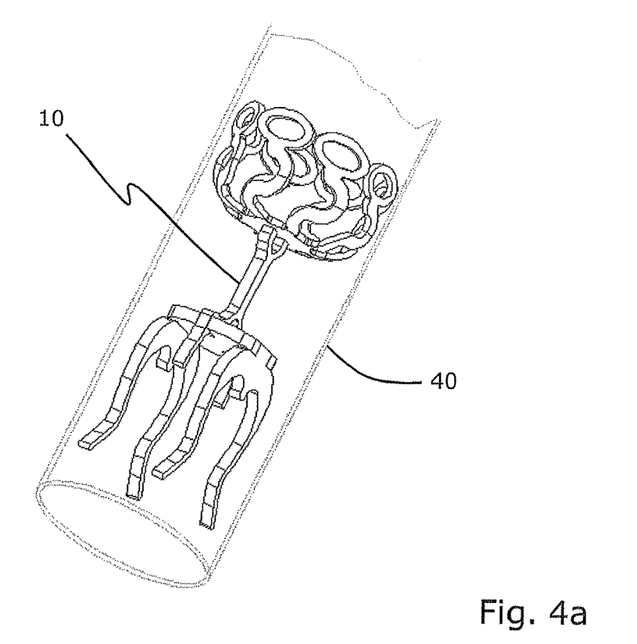
FIG. 4a shows a spatial representation of the embodiment according to FIG. 1a, in the folded-up state of the bridging elements, within a tubular hollow body which is transparent in this representation.
Figure 4B:
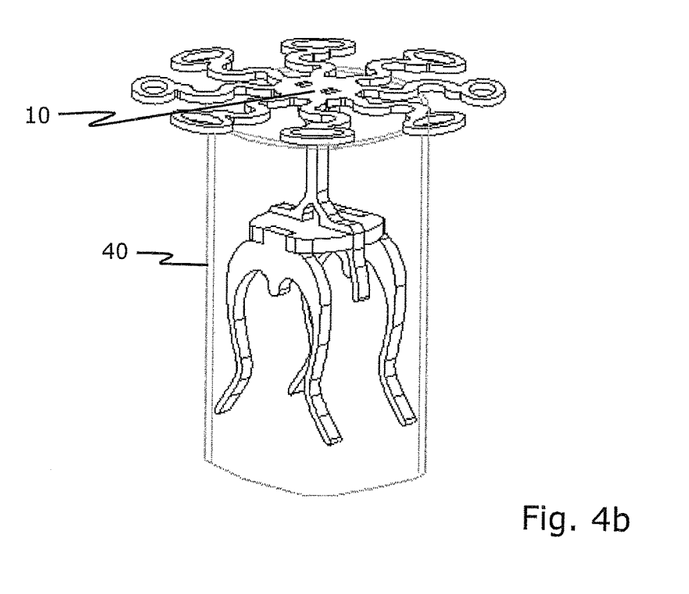
FIG. 4b shows the arrangement according to FIG. 4a including the head plate extending out of the tube, wherein the bridging elements are in the state without force introduction.

Finally, FIGS. 4a and 4b show a system which includes the embodiment of the ossicular prosthesis 10 according to the invention according to FIG. 1a, and an implantation aid comprising an elongate hollow body 40 which is open on at least one side, the system being distinguished by the fact that the internal width of the hollow body 40 is selected in such a way that the ossicular prosthesis 10, in a state with introduction of force onto the bridging elements 15, can be accommodated entirely or partially in the hollow body 40. Generally, the hollow body 40 is in the form of a minimally invasive, in particular endoscopic, instrument, which is preferably tubular or hose-shaped. By means of this implantation aid, the ossicular prosthesis 10; 20; 30 according to the invention can be easily introduced into the human middle ear.

In this case, FIG. 4a illustrates how the ossicular prosthesis 10, in the folded-up state of the bridging elements 15, is accommodated within a tubular hollow body 40, which is transparent in this representation, with the aid of which tubular hollow body the prosthesis can be inserted into the middle ear through an—in particular artificially created—opening, which has a minimal diameter. In this "insertion state", forces having force components parallel or antiparallel to the longitudinal axis z, which are imparted by the inner wall of the hollow body, act upon the bridging elements and cause them to fold upward due to the elasticity of the bridging elements (and/or due to corresponding articulations).

FIG. 4b shows the arrangement according to FIG. 4a, with a head plate of the ossicular prosthesis 10 extending from the tube 40, wherein the bridging elements 15—as is the case after the implantation in the middle ear—are now in a state without force introduction and are therefore unfolded in the manner of an umbrella, radially away from the longitudinal axis z.

What is claimed is:

1. An auditory system comprising:
an ossicular prosthesis which is adapted to replace or bridge at least one member or parts of a member of the ossicular chain, and
an implantation aid comprising an elongate tubular or hose-shaped endoscopic instrument sized and configured to introduce the ossicular prosthesis into a human middle ear,
wherein the ossicular prosthesis comprises:
a first fastening element at one end of the prosthesis, in the form of a head plate which is intended to mechanically rest against the tympanic membrane and/or against the malleus handle, wherein the first fastening element substantially replicates the anatomical shape of the tympanic membrane;
a second fastening element at another end of the prosthesis for the mechanical connection to one member or parts of a member of the ossicular chain, or to the inner ear,
an elongated connecting element which connects the two fastening elements to one another in a sound-conducting manner along a longitudinal axis (z),
wherein the head plate comprises a radially inner coupling region situated centrally with respect to the longitudinal axis (z) for the mechanical coupling of the head plate to the connecting element, and multiple bridging elements extending outwardly from a central coupling region and radially away from the longitudinal axis (z), each of said bridging elements being connected to the central coupling region via a radially inner end region and transitioning into a radially outer, free end section,
wherein the bridging elements are connected, at their radially inner end regions, to the central coupling region in such a way that the bridging elements fold upward or downward, in the manner of an umbrella, in the direction of the longitudinal axis (z) upon introduction of a force having a force component parallel or antiparallel to the longitudinal axis (z), wherein the radially outer, free end sections are each pivoted, relative to the longitudinal axis(z), toward a position located radially closer to the longitudinal axis(z) and thereby also execute an axial movement relative to the longitudinal axis (z), and the bridging elements, without introduction of the force, extend from the central coupling region at a predefined, fixed angle relative to the longitudinal axis (z),
wherein each of the bridging elements extends between the central coupling region and its radially outer, free end section in the shape of a multiply deflected curve,
wherein each of the radially outer, free end sections is formed as a closed or annular end section, having a circular or elliptical configuration, which is adapted to expand transversely relative to the direction of the longitudinal axis (z), wherein at least the bridging elements are formed from an elastic, flexible material, wherein an internal diameter of the tubular or hose-shaped endoscopic instrument is selected in such a way that the ossicular prosthesis, in a state with introduction of force onto the bridging elements, can be accommodated entirely in the tubular or hose-shaped endoscopic instrument with the bridging elements folded upward or downward, in the manner of an umbrella, in the direction of the longitudinal axis (z).

2. The auditory system according to claim 1, wherein the bridging elements, in a state without introduction of force, extend from the central coupling region in an angle range relative to the longitudinal axis (z) of between 80° and 100°.

3. The auditory system according to claim 2, wherein the bridging elements extend from the central coupling region at an angle of approximately 90° relative to the longitudinal axis (z).

4. The auditory system according to claim 1, wherein the bridging elements, in a state without introduction of force, extend from the central coupling region at different, predefined angles relative to the longitudinal axis (z).

5. The auditory system according to claim 1, wherein the elastic, flexible material has an elasticity of ≥1%.

6. The auditory system according to claim 5, wherein the elastic, flexible material contains highly elastic material in the form of amorphous metal based on nickel, iron, cobalt, or zirconium, and/or a nickel/titanium alloy.

7. The auditory system according to claim 5, wherein the elastic, flexible material contains a high-strength elastic polymer, and/or elasticceramic.

8. The auditory system according to claim 5, wherein the elastic, flexible material has an elasticity of ≥2%.

9. The auditory system according to claim 1, wherein the radially outer, free end sections of the bridging elements are formed as atraumatic surfaces.

* * * * *